(12) United States Patent
Pilloud et al.

(10) Patent No.: US 7,242,463 B2
(45) Date of Patent: Jul. 10, 2007

(54) METHOD AND DEVICE FOR DETECTING PATTERNS ON A SUBSTRATE

(75) Inventors: Francis Pilloud, Clarens (CH); Patrick Servet, Cugy (CH)

(73) Assignee: BOBST S.A. (CH)

( * ) Notice: Subject to any disclaimer, the term of this patent is extended or adjusted under 35 U.S.C. 154(b) by 205 days.

(21) Appl. No.: 11/116,526

(22) Filed: Apr. 28, 2005

(65) Prior Publication Data

US 2005/0248767 A1 Nov. 10, 2005

(30) Foreign Application Priority Data

May 5, 2004 (CH) .................................. 0800/04

(51) Int. Cl.
*G06K 9/74* (2006.01)
(52) U.S. Cl. ...................... 356/71; 356/429; 235/380; 235/454
(58) Field of Classification Search ............... 250/559.1–559.46; 356/426–431, 71, 603–604, 356/458–459; 235/375, 435, 380, 454
See application file for complete search history.

(56) References Cited

U.S. PATENT DOCUMENTS 5,225,886 A * 7/1993 Koizumi et al. ......... 356/237.4

| | | | |
|---|---|---|---|
| 5,486,254 A | 1/1996 | Gallagher et al. | 156/229 |
| 5,823,692 A | 10/1998 | Tolrud et al. | 400/582 |
| 6,291,829 B1 | 9/2001 | Allen et al. | 250/559.07 |

OTHER PUBLICATIONS

European Search Report EP 04 40 5286 dated Oct. 8, 2004.

* cited by examiner

*Primary Examiner*—N. Drew Richards
*Assistant Examiner*—Tara S. Pajoohi
(74) *Attorney, Agent, or Firm*—Ostrolenk, Faber, Gerb & Soffen, LLP

(57) ABSTRACT

Device for detecting patterns on a travelling substrate, namely on a substrate being deposited on a sheet or on web matter, wherein the substrate is a metallized foil travelling in a travelling direction. The device comprises a housing for a first incidental beam issued from a first source of light, a second incidental beam issued from a second source of light, an optical measuring system, a photosensitive sensor respectively delivering beams reflected from the substrate and an electronic unit connected to a communication port. The optical measuring system is telecentric, the first incidental beam crosses a telecentric lighting system and the second incidental beam crosses an oblique lighting system.

8 Claims, 3 Drawing Sheets

METHOD AND DEVICE FOR DETECTING PATTERNS ON A SUBSTRATE

BACKGROUND OF THE INVENTION

The present invention refers to a method and a device for detecting patterns on a travelling substrate, in particular on a substrate being deposited on a foil or sheet matter.

Such substrates usually consisting of stamping foils. The substrates are intended for being deposited on sheet or foil matter, which are, for example, used in the packaging industry for applying metallic foils on blanks or on any other sheet or foil material. That operation can typically be carried out either in a platen press, or a rotary press or any other processing machine, by means of a stamping foil and printing plates that are, together with the processable sheet or foil matter, pressed against one another between upper and lower tools of the press or of the processing machine. Under the pressure generated in the presses or processing machines, a stamping foil portion is thus diecut and deposited by heat-sealing on the sheet or foil matter. U.S. Pat. No. 5,486,254 describes in more detail one of the presses and namely a device enabling registering pre-printed patterns on a foil with patterns of a stamping press.

There are plenty of types of stamping foils, among which are the reflective plain specular foils, the holographic diffraction foils and the reflective structured foils. The latter are of iridescent and variable effect offering patterns more or less visible depending on the angle at which one observes them.

The regular plain foils are usually uniform from one end to the other and do not comprise any specific pattern. They can thus be processed into the press without worrying about a specific printing mark location. Only an optimal use of the matter aiming to reduce the waste will be the main feature taken into account for defining the foil travel.

For hologram foils, the machine operator must be able to ensure that the foil travel is perfectly controlled so that the patterns, i.e. holograms, are at any time in perfect register with the printing plates applying them on plate elements. Even a slight shift is not allowed because the pattern would thus be altered or it would cause an eccentric application of the hologram.

when using so called structured foils, it is advisable to ensure that foil portions are contrarily not applied by the patterns. Such foils effectively comprise connections regularly distributed each 50 or 60 cm, for example. The connections depend on the foil manufacturing embodiment itself. They are issued from the decorative metallic layer printing on the supporting foil. Since printing is processed in a rotary press equipped with a cylindrical printing plate supporting the geometrical structure to print, this produces a fine transverse line of the order of one or a few tens of mm. width to appear on the foil at each revolution of the printing cylinder. That connection is directly issued from the cylindrical printing plate which has a pattern that can obviously not cover the entire 360° of the cylinder.

Such foil connections can also appear on holographic foils. When the space between two connections is not related to a pitch multiple of the foil holograms, it is quite obvious that one holographic pattern will unfortunately step over a connection. When manufacturing high quality packaging, it is not admissible that a holographic pattern crossed by a connection is deposited on a packaging box blank. In such a case, one will have to switch the holographic pattern and deposit the next one.

Using the word pattern, one understands here and in the whole following specification, that it can either be a hologram pre-printed on the foil, or a foil connection or a transition between two substrates of different structure, as well as a register mark or even the imprint left by the pattern on the plate-like element. From time to time, one ensures that the pattern, i.e. a holographic pattern, is in perfect register with the printing plates, although in other cases, one will on the contrary ensure that the pattern, i.e. a foil connection, is effectively never stamped by the patterns on plate-like elements.

It is known to use foil scanning devices enabling detecting, before stamping, the threading of such a pattern and then consequently modifying the stamping foil travel. Such scanning devices comprise at least one foil lighting unit, an objective and a photoelectric sensor which translates the intensity of the light reflected by the foil into an answer signal.

The goals of the devices are conventionally simple and have each foil portion pitch to be examined under a different angle varying also according to the measure spacing, i.e. according to the distance between the objective related to the foil plan. The scanning devices are also equipped with one or two symmetrical lights, external to the measuring optical and bent with respect to the optical axis of measure. If such devices are well adapted for scanning diffusing foils wherein the light is precisely diffused into the entire solid angle formed by the two lights, they become on the other hand inappropriate for scanning specular foils wherein the light is reflected apart the opening of the measuring optical.

In other cases, the lighting device external to the measuring optical comprises a semi-transparent mirror arranged at 45° in front of the objective, as well as a source of light located perpendicularly to the measuring axis. The source of light, partially reflected by the blade, lights the foil according to the same axis than the optical measuring system. If the substrate is metallized, the reflected light travels back in the direction of the objective, one part reflected by the semi-transparent blade is lost, and the second part enters the objective and enables measuring. When using diffusing substrates, a large part of the incident light is diffused in all directions after reflection and only a very tiny part is sent back towards the objective. That returning part is not or only very little depending on the light incidence angle. It is thus not necessary for the light to be in the same axis than the axis of the measuring optical. One will rather try to get a light of a maximum intensity which is often easier to obtain with an indirect light.

With matrix systems, there are lighting devices associating at the same time a direct light, perpendicular to the foil plane, and an indirect light, arranged crosswise according to that plane. However, as those lighting devices are very large in dimensions, the sensors including at the same time a measuring unit as well as a lighting unit comprise a simple measuring objective, as previously described, as well as a less performing lighting system, either of indistinct type or direct type. The photoelectric sensors connected to these cameras are intended to deliver images of a foil portion with a surface usually equivalent to several thousands of pixels. Such sensors generate thus a huge quantity of images data which are hard to process because of short times.

Among the various sensors known to date, one notices that the ones having the best signal-to-noise ratio with structured foils, become unreliable when using other foil types with specular effect. No sensor today enables treating efficiently and reliably all foil types, either metallized or not, diffusing, structured, refracting or diffracting. The preferred solution today aims to provide at least two sensors in the platen press, one dedicated, for example, to structured foils and the other more specifically to all other foil types. It is then necessary to manually switch over to one or the other sensor according to the type of foil used. Because the average cost for such a sensor is already almost high, such a solution is thus economically not very convenient.

Another drawback of the known devices consists in that the choice of a preferred light in accordance with the substrate used will often depend on the know-how of the machine operator as well as on results of multiple tests. Moreover, the answer quality delivered by the sensor will also vary with respect to the angular positioning of the lighting devices and the scanning device according to the foil plan. A bad setting will not enable reaching a sufficiently contrasted signal-to-noise ratio ensuring detecting the threading of a requested pattern, all the more when the foil bottom is structured and comprises for example a plurality of false interconnected pattern.

With the recent use of structured foils, it is particularly difficult for the current sensors to differentiate the foil connection from an edge of a geometrical shape constituting the structured foil bottom. When the latter is checkered, for example, it becomes particularly difficult to detect a pattern, like a foil connection, since the signal-to-noise ratio delivered by the sensor is not sufficiently well-marked.

SUMMARY OF THE INVENTION

The object of the present invention is to avoid the above drawbacks by providing a device for detecting patterns enabling to scan patterns on substrates, such as stamping foils, of any type. The detection device must be easy to put into operation. It must not need any specific setting operation, whatever type of foil used, and it must not require manual settings during the calibration phase. The present invention refers also to an automated detection method, related to said device.

These aims are achieved owing to the present invention of a device for detecting patterns on a travelling substrate, namely on a substrate being deposited on a sheet or on web matter, wherein the substrate is a metallized foil travelling in a travelling direction. The device comprises a housing for a first incidental beam issued from a first source of light, a second incidental beam issued from a second source of light, an optical measuring system, a photosensitive sensor respectively delivering beams reflected from the substrate and an electronic unit connected to a communication port. The optical measuring system is telecentric, the first incidental beam crosses a telecentric lighting system and the second incidental beam crosses an oblique lighting system.

Other features and advantages of the present invention will become apparent from the following description of the invention which refers to the accompanying drawings.

BRIEF DESCRIPTION OF THE DRAWINGS

The invention will be more clearly understood from the study of a preferred embodiment given by way of non-limitative example and illustrated by the accompanying drawings, in which.

DESCRIPTION OF A PREFERRED EMBODIMENT

Figure 1:
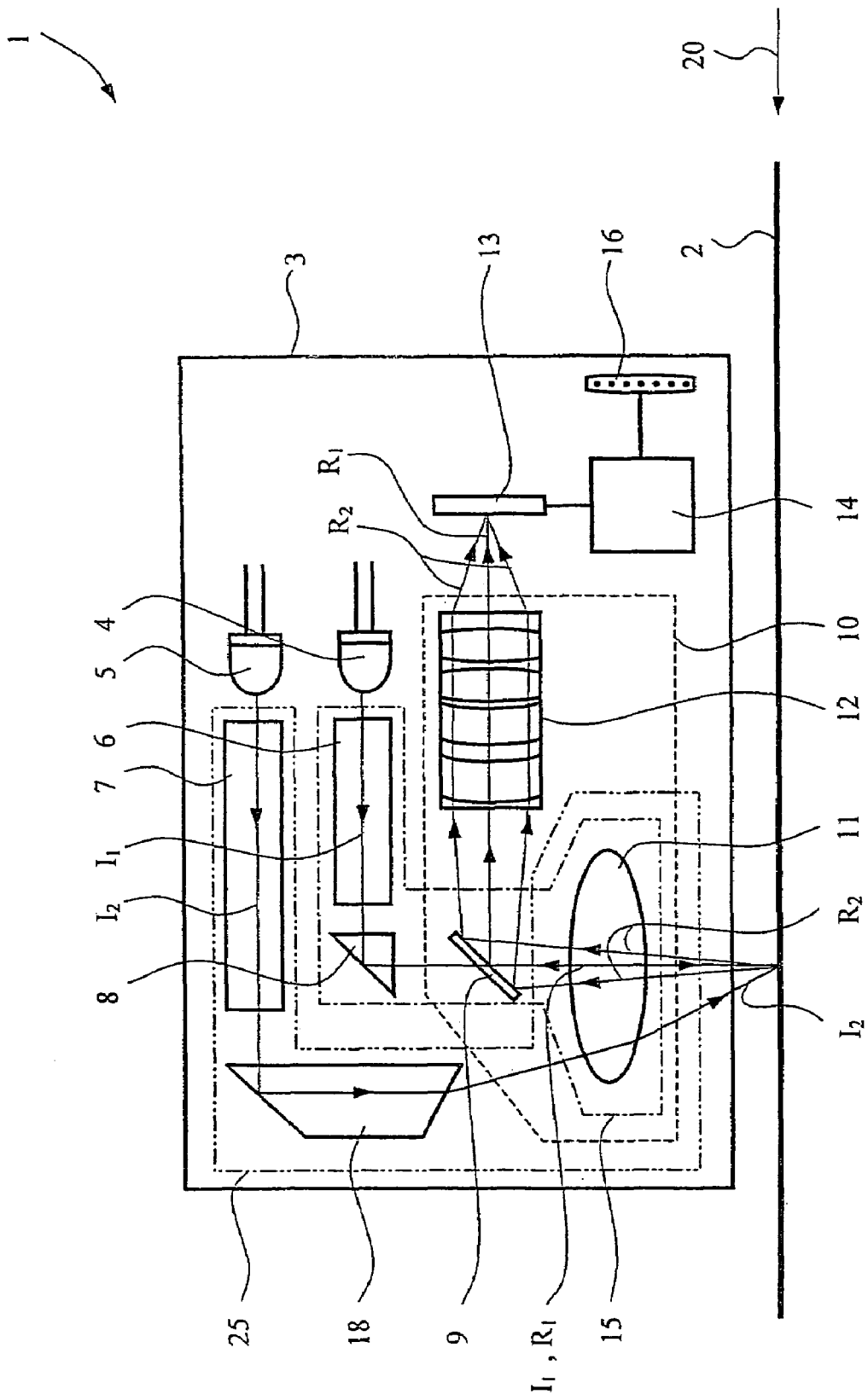
FIG. 1 is a schematic view of the detection device of the invention.

FIG. 1 is a schematic view of the device 1 for detecting patterns on a travelling substrate 2, being deposited on a foil or sheet matter, wherein the substrate travels through a driving means in a travelling direction 20 illustrated by a corresponding arrow. The detection device 1 is enclosed in a housing 3. The device comprises at least a first source of light 4 and a second source of light 5, each source possibly generating a light of at least two colors, preferably a first color like blue and a second color like red. The color choice is preferably based on colors being relatively spaced the one another in the visible spectrum, in order to improve the measuring result and more particularly to increase the contrast of the delivered image. The sources of light 4, 5 each emit a first incidental beam $I_1$ and a second incidental beam $I_2$. Each beam respectively enters a first and a second optical unit 6, 7 which may be a homogenizer, a mixer or a light condenser, even more than one thereof, or a combination of several filters, for example.

The first incidental beam $I_1$ issues from the first source and is deviated towards the substrate 2 by a first deviation unit 8, such as a prism or a mirror with an equivalent function, for example. That first incidental beam then enters an optical measuring system 10 and in particular a first optical system 11, after it crosses a semi-transparent deviation blade 9. The optical measuring system 10 constitutes the objective of the detection device 1, whereas the first optical system 11 involves only a part of it. The system 11 is possibly a lens or a combination of several lenses, constituting a doublet, for example.

The combination formed by the first optical system 11, the semi-transparent deviation blade 9, the first deviation unit 8 and the first optical unit 6, constitutes a telecentric lighting system 15. The telecentric feature of the lighting system means that the first incidental beam $I_1$ strikes the substrate 2 parallel to a standard line of the substrate and because of the specular feature of said substrate, the beam is sent back in the opposite direction along the optical axis of the optical measuring system 10. The optical measuring system 10 comprises the first optical system 11, which is commonly used for lighting as well as for delivering the beam reflected by the substrate 2, and a second optical device 12. The system 10 is conceived to form a telecentric optical measuring device, i.e. a device wherein the rays of the luminous beam are arranged slightly parallel to one another as well as perpendicular with respect to the surface to be lit.

According to the arrangement of the different units forming the detection device 1, one will note that the telecentric lighting system 15 could be reduced to a combination between the first optical system 11 and the semi-transparent deviation blade 9. This particular case would refer to another embodiment of the first source of light 4, wherein the source is thus aligned with the optical axis of the first optical system 11, i.e. according to a perpendicular position with respect to the plane of the substrate 2.

From the exit of the first optical system 11, the first incidental beam $I_1$ will light the substrate, perpendicularly to its plane. If the substrate comprises a specular upper surface, the first incidental beam would then be upwardly reflected, perpendicularly to the substrate plane. From that time, the first incidental beam reflected by the substrate will thus be a so called first reflected beam R1. That reflected beam R1 will then meet the semi-transparent deviation blade 9 a second time, but this time from the bottom, and will be partly reflected towards a second optical system 12. The second optical system 12 is also included in the optical measuring system 10 and constitutes thus another part of the objective of the detection device 1. As illustrated on FIG. 1, the second optical system 12 is preferably made of a plurality of lenses such as a triplet or a more specific assembly. Lastly, from the exit of the optical measuring system 10, the first reflected beam R1 strikes perpendicularly a photosensitive sensor 13. According to a preferred embodiment, that sensor is advantageously a linear photosensitive one, of type CMOS or CCD, which produces an image of a transverse portion of the substrate 2 with respect to its travel direction 20.

Referring to the second incidental beam $I_2$ issued from the second light source 5, one notes on FIG. 1 that the beam $I_2$ is also deviated at the exit of the optical device 7 through a second deviation device 18 which is a prism or an equivalent set of mirrors. The travel path of the second incidental beam $I_2$ is such that it then enters the first optical system under an incidence angle not equal to zero with respect to the optical axis of said system. That angle of incidence is typically of the order of 10 to 40 degrees. From the exit of the first optical device 11, the incidental beam $I_2$ travels towards the substrate 2 until it stops at the substrate in the focal plane of the first optical system 11. The focal plane is thus mixed up with the one of the substrate 2, more particularly with the travel plane of the substrate. The combination comprising the first optical device 11, the second deviation unit 18 and the second optical unit 7 constitutes an oblique lighting system 25. The oblique feature relates to the incidence angle at which the second beam $I_2$ strikes the substrate 2 with respect to the substrate standard.

According to the arrangement of the different units comprised in the detection device 1, the oblique lighting system 25 could be reduced to a single first optical system 11, even to a combination of the first optical system with the second deviation unit 18. That specific case would refer to another embodiment of the second source of light 5, which will thus be located in a vertical plane that is slanted with respect to the optical axis of the first optical system 11.

If the upper surface of the substrate is diffusing, diffracting or holographic, the second incidental beam $I_2$ is thus be diffused or diffracted in all directions above the travel plane of the substrate. Part of the diffused reflection is sent back in the direction of the optical measuring device 10 and enters the first optical system 11. The reflected beam portion located in the vicinity of the optical axis of the first optical system 11 constitutes the second reflected beam R. That beam will then be partly reflected by the semi-transparent deviation blade 9 towards the second optical system 12. From the exit of the second optical system 12, the second reflected beam $R_2$ finally strikes the surface of the photosensitive sensor 13 at the meeting point of the first beam $R_1$.

The intensity of the reflected beams $R_1$, $R_2$ is moderated by the reflection variations of the substrate. That intensity is transformed by the photosensitive sensor into a signal or information intended to be sent to an electronic unit 14. That unit comprises at least a memory and a computer such as a microprocessor. The electronic unit 14 aims also to control the activation of the units of the detection device 1, namely the start up of the different light combinations provided by the choice of colors as well as the choice of the lighting systems 15, 25 used.

In order to deal with the provided data or the one that will travel through the electronic device 14, the device 14 is still connected to a communication port 16. The communication port makes it possible to export data towards other processors, namely enabling final control of the driving means of the substrate 2 and supervising the travel of the substrate. The communication port 16 is also useful because it enables on the contrary importing data or orders aiming, for example, to adapt the detection method applied to the detection device 1.

Figure 2:
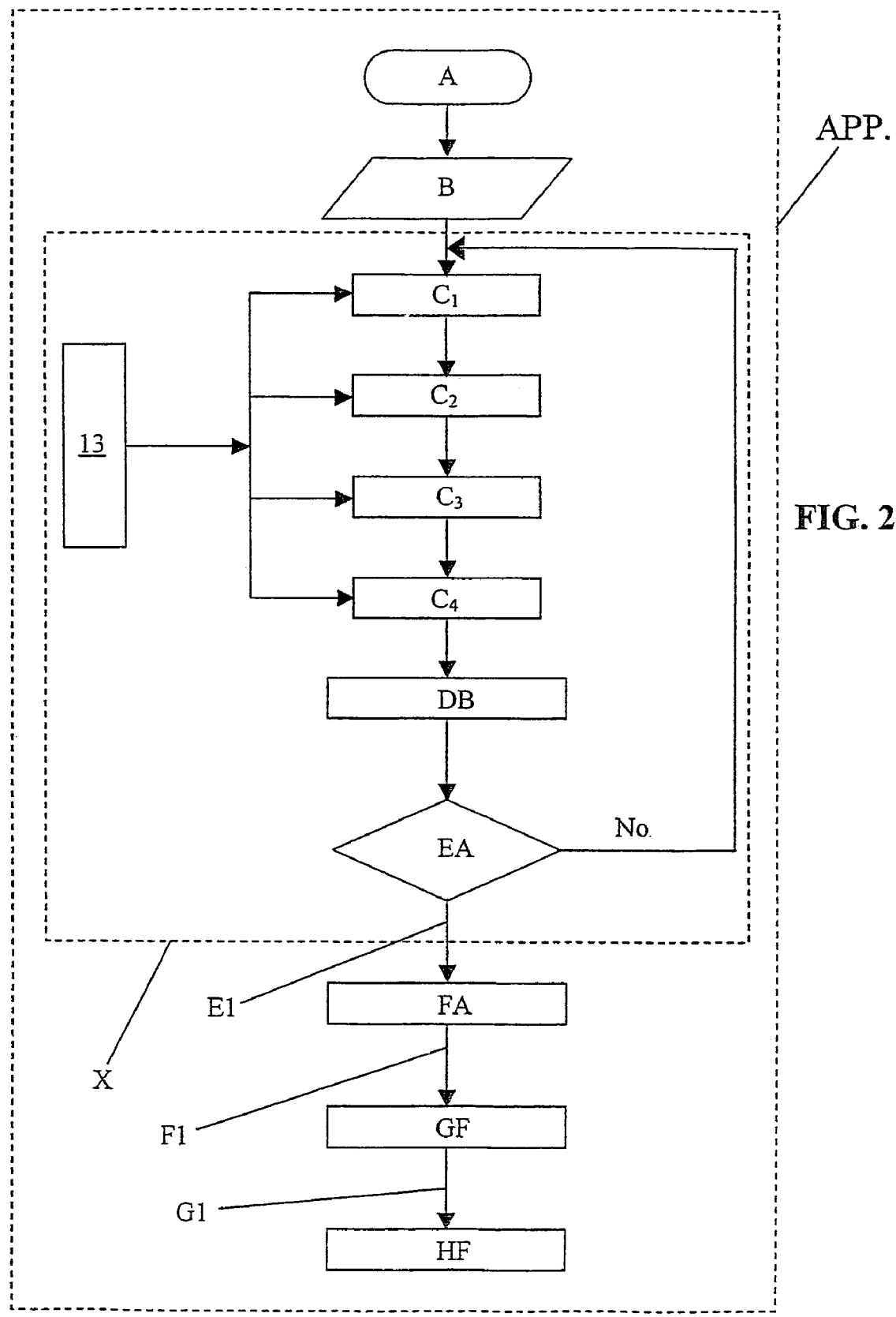
FIG. 2 shows a flow diagram illustrating the detection method applied during the training phase of FIG. 1 device.

FIG. 2 shows a flow diagram illustrating the detection method applied in the training phase of FIG. 1 device. That training phase begins with a first stage A. Afterwards, in a second stage B, one observes the travelling matter foil, and define a number of lines L1 to Ln to be scanned, and thus on a distance related to the existing center distance of the axis between two patterns or, in case of a foil connection detection, on a distance related to the one between two connections, this enables thus defining the lines number of each expected light condition to be reached during a detection cycle. The conditions are each obtained by starting up one of the sources of light 4, 5 of determined color. With two light colors, for example blue and red, and with two possible light ways, a first one crossing the telecentric lighting device 15 and a second one entering the oblique lighting device 25, one reaches in that case, for example, four different light conditions, plus one for the turned off LED condition, not shown on FIG. 2.

One defines third stages C1 to Cn and D, for which lines L1 to Ln, successively registered by the photosensitive sensor 13, will be illuminated according to predetermined light conditions. The lines L1 to Ln are then processed separately to form an image related to each predetermined light condition.

In a fourth stage, one also stores, the image of lines L1 to L4 scanned by the photosensitive sensor 13 during stages C1 to C4 and D. This is done as many times as is necessary to reach the Ln lines number related to the distance between two patterns or successive connections, i.e. by carrying out as many times as necessary the X loop including stages C1 to C4, D and E. Once the lines number to reach for each light condition is determined, one will obtain an E1 data related to lines L1 to L4 images, under each different light condition, of the substrate portion to examine, i.e. in that present case, four different images.

The E1 data is separately processed in a fifth stage F in order to define which will be the optimal light and to define the P1 to Pn associated parameters such as, for example, the value of a detection threshold for objects or connections, or parameters related to the substrate, object or connection to detect. At the exit of stage F, one has selected the optimal light to use as well as its associated detection threshold. That data is represented by a value F1, stored in a sixth stage G.

The collected F1 values will be safeguarded and stored into the photosensitive sensor 13 memory and the exit value G1 of stage G will be introduced in a seventh stage H, consisting in memorizing and safeguarding P1 to Pn parameters as well as the detection threshold value of the pattern or the connection to detect. This will determine the beginning of the production operating phase of the detection of patterns or connections by the processing machine. The whole training phase is represented by the APP reference.

Figure 3:
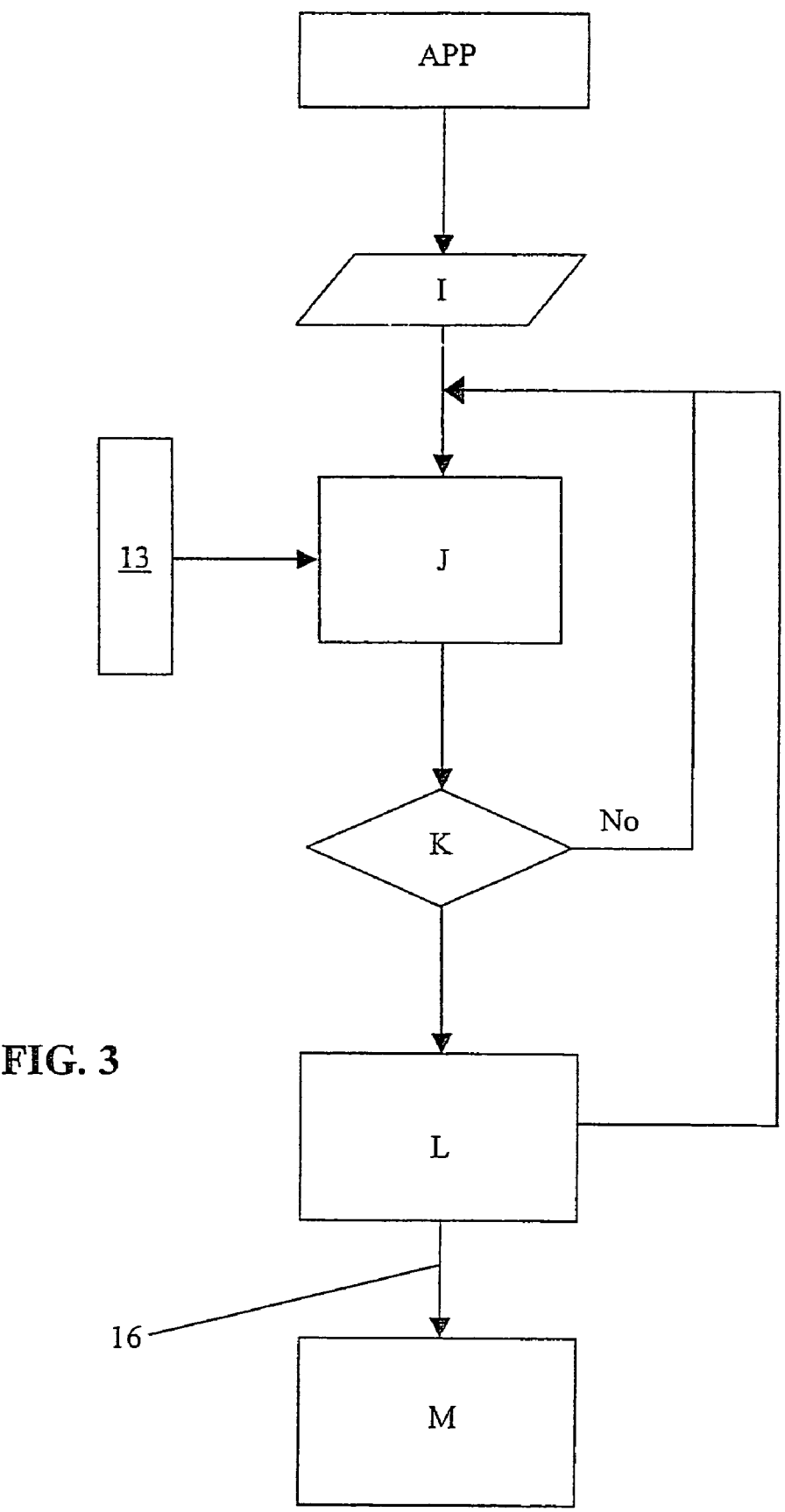
FIG. 3 shows a flow diagram illustrating the detection method applied in the processing phase of FIG. 1 device.

FIG. 3 shows a flow diagram illustrating the applied method in the production operating phase of FIG. 1 device. The production operating phase of detection device 1 begins with loading, in an eighth stage I, P1 to Pn parameters and the detection threshold value delivered in the training phase APP.

Then, one watches the substrate, i.e. the travelling matter foil, by means of the photosensitive sensor 13 and, in a ninth stage J, one compares the result of that studying or scanning of the matter foil with the detection threshold of the training phase APP. That comparison results in a data, treated in a tenth stage K, that will give a signal value larger or smaller than the detection threshold value. In case the signal value resulting from stage K is smaller than the one of the detection threshold, said treatment will be restarted, since that condition means that no pattern or connection was detected. In case the signal value resulting from stage K is larger than the one of the detection threshold, one is dealing with either a pattern or a connection, and the signal resulting from stage K will be sent to the machine interface M during an eleventh stage L through the communication port 16. The detection device 1 works continuously during the whole operating phase of the processing machine, until a job change. At the time of such a change, a new training APP phase will start, followed by a new production operating phase.

As an alternative, the detection device 1 could comprise more than two light sources. Each source is possibly a source of LED type, which is able to produce a light of two or three different colors. The number of possible colors is not restricted to two or three. Moreover, the colors could be obtained either by light sources that directly produce a colored light or by a combination of a white color source associated with one or more colored filters. One will still point out that the number of possible colors conditions directly the number of possible light combinations.

As an alternative, the second deviation unit 18 could be swivellingly adjustable. It would thus become possible to choose the optimal incidence angle for the substrate light by means of the transverse lighting system.

The above mentioned detection device 1 makes it possible to detect efficiently and with high reliability any type of pattern on any type of substrate. Indeed, in case the substrate surface is specular, plain or structured, one prefers using the telecentric lighting system 15 for detecting the pattern and in particular the intensity differences between the reflected beam $R_1$ on the pattern and the beam applied on the substrate bottom. Inversely, to detect a pattern on a substrate having a diffuse decorative surface or when the pattern is formed by a surface with diffractive effect, one prefers using the transverse lighting system 25, so as to obtain a better signal-to-noise ratio. Moreover, in order to improve the contrast of the image provided by the photosensitive sensor, it is still possible to choose a light of specific color, and this for each of both described lighting modes.

One can note that in that process, it is not necessary to determine the most convenient light combination for detecting a selected pattern on an unspecified substrate. The method of the present invention advantageously enables carrying out the determination on a foil length as short as possible. In case of the use of structured foils or foils printed by a cylinder, that length relates to the distance between two consecutive patterns or connections. Material losses as well as time needed for setting and calibrating the detection device are thus further reduced.

The processing speed of the image provided by the photosensitive sensor 13 enables the detection device 1 to carry out substrate registering in a sufficiently short time so that it is possible to proceed to all comparisons of the different lights during the travelling of one single pattern or connection. That processing speed is also due to the fact that it was intended for joining a photosensitive sensor 13 of linear type. That sensor type makes it possible to obtain an image that can be translated into a data being at the same time reliable and far from bulky. On the contrary, in case of using a monopixel sensor, the delivered data cannot be considered as sufficiently reliable since a single defect in the substrate surface could be considered as a pattern detection, whereas it is in fact not the case. Inversely, using sensors restoring a surface of several hundreds or thousands of pixels becomes a bulky data that will have to be processed in an obviously more significant time. The answer delays will thus be longer and it will thus all the more decrease the performance of the device.

Advantageously, thanks to the telecentric feature of the lighting and measuring system, the size of the object to control does not vary according to its location in the objective field of the detection device, and in particular according to its distance.

More advantageously, the sharing of some optical components, such as the first optical system 11 and the semi-transparent deviation blade 9, while processing with several functions, as the one of the lighting systems telecentric 15 and transverse 25 as well as the one of the optical measuring system 10 makes it possible to reduce the number of units of the detection device 1 and to reduce the size of the housing 3.

By combining two lighting ways included in the same housing 3 of the detection device, any manual setting of the light angle with respect to the substrate becomes useless. It is thus sufficient to place the housing in a single position, for example horizontal according to the relative positions of the substrate and the objective, so that the detection device is correctly arranged. It generates a time saving during the machine preparation as well as the insurance to benefit at any time of an optimal light angle.

Although it is expected for the method to choose a lighting combination without any selection order, it is obviously usually expected to achieve the selection according to a specific order, previously defined. The selection order is also defined and stored in the electronic device 14.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A device for detecting patterns on a travelling substrate travelling in a travel direction, comprising:
    a housing;
    a first source of light issuing a first incidental beam toward the substrate;
    a second source of light issuing a second incidental beam toward the substrate;
    an optical measuring system, a photosensitive sensor respectively collecting reflected beams from the substrate wherein the optical measuring system is telecentric, the first incidental beam crosses a telecentric lighting system and the second incidental beam crosses an oblique lighting system; and
    an electronic unit connected to the sensor and connected to a communication port.

2. The detection device according to claim 1, wherein the optical measuring system comprises a semi transparent deviation blade;
    a first optical system crossed by the first and the second incidental beams and the respective first and second reflected beams generated by the first and second incidental beams;
    a semi-transparent deviation blade; and
    a second optical system positioned to be crossed only by the first and second reflected beams after they have been reflected on the semi-transparent deviation blade.

3. The detection device according to claim 2, wherein the telecentric lighting system comprises the semi-transparent deviation blade and the first optical system, and the first optical system comprises the oblique lighting system.

4. The detection device according to claim 1, wherein the photosensitive sensor is a linear photosensitive sensor operable to produce an image of a transverse portion of the substrate with respect to the travel direction.

5. The detection device according to claim 1, wherein the first source of light and the second source of light each produce a light of at least one first color and one second color.

6. The detection device according to claim 1, wherein the first color is blue and the second color is red.

7. The detection device according to claim 3, wherein the oblique light system comprises a second deviation unit from the second incidental beam and the second deviation unit is swivellingly adjustable with respect to the second incidental beam.

8. A device for detecting patterns on a travelling substrate travelling in a travel direction, comprising:
   a housing;
   a first source of light issuing a first incidental beam toward the substrate;
   a second source of light issuing a second incidental beam toward the substrate;
   a first beam deflector shaped and positioned for deflecting the beam from the first source of light telecentrically on an axis toward the substrate;
   a second beam deflector shaped and positioned to deflect the beam from the second source of light obliquely of the axis and toward the substrate;
   a deflection blade positioned for deflecting the reflected light from the substrate, supplied by the first and the second light sources, toward an optical system;
   an optical measuring system, a photosensitive sensor respectively collecting reflected beams from the substrate wherein the optical measuring system is telecentric, the first incidental beam crosses a telecentric lighting system and the second incidental beam crosses an oblique lighting system; and
   an electronic unit connected to the sensor and connected to a communication port.

* * * * *